(12) United States Patent
Watson et al.

(10) Patent No.: US 6,468,525 B1
(45) Date of Patent: Oct. 22, 2002

(54) PROBIOTIC FORMULATION

(75) Inventors: Tommy Stanley Watson, Tarpon Springs, FL (US); Brenda F. Watson, Tarpon Springs, FL (US)

(73) Assignee: Renew Life, Inc., Clearwater, FL (US)

( * ) Notice: Subject to any disclaimer, the term of this patent is extended or adjusted under 35 U.S.C. 154(b) by 0 days.

(21) Appl. No.: 09/371,335

(22) Filed: Aug. 10, 1999

(51) Int. Cl.⁷ .................................. C12N 1/20
(52) U.S. Cl. .................. 424/93.3; 424/93.45; 435/243; 435/252.4
(58) Field of Search ............. 424/93.3, 93.45; 435/243, 252.4

(56) References Cited

U.S. PATENT DOCUMENTS

| | | | | |
|---|---|---|---|---|
| 5,164,183 A | * | 11/1992 | Komoda et al. | |
| 5,310,555 A | * | 5/1994 | Zimmer | |
| 5,322,836 A | * | 6/1994 | Tomita et al. | |
| 5,531,989 A | * | 7/1996 | Paul | |

* cited by examiner

Primary Examiner—Leon B. Lankford, Jr.
Assistant Examiner—Susan D. Coe
(74) Attorney, Agent, or Firm—Donald R. Fraser

(57) ABSTRACT

A probiotic formulation, useful as a food supplement and a material for reestablishing beneficial bacteria to the body's intestinal tract, comprises a mixture of beneficial probiotic microflora comprising lactobacillus acidophilus, bifidobacterium bifidum, lactobacillus salivarius, bifidobacterium infantis, and bifidobacterium longum, fructooligosaccharides, L-glutamine, and N-acetyl glucosamine.

18 Claims, No Drawings

PROBIOTIC FORMULATION

FIELD OF THE INVENTION

The present invention relates generally to a probiotic formulation. More particularly, the invention is directed to a food supplement formulation comprising five specific microflora and additional ingredients which work together to support the body's ability to replace mucosal linings such as those found in the digestive tract.

BACKGROUND OF THE INVENTION

Probiotic formulations have been used as dietary supplements for many years. Hundreds of different strains of probiotics exist, but only a select few (about 50) of these strains have been tested for efficacy. Beneficial probiotics are categorized as either resident or transient. Resident probiotic bacterial strains live and reproduce in each person's digestive tract. Transient probiotic bacterial strains typically are introduced into the body through ingested food or by means of dietary supplements; however, they do not reproduce nor stay within the digestive system. Probiotic bacteria which normally inhabit the digestive tract reduce the levels of harmful bacteria which may be introduced to the body. For example, naturally occurring probiotic bacteria reduce levels of E. Coli and Salmonella by producing metabolic acid products, e.g., hydrogen peroxide, lactic acid, and acetic acid, that inhibit or antagonize these harmful bacteria. Probiotics also inhibit the levels of harmful microbial pathogens, by lowering the pH in the intestines. This production of organic acids effectively lowers intestinal pH to a level that is favorable for beneficial bacteria and destructive to pathogens. Probiotic bacteria also prevent the establishment of harmful fungus and parasites, such as Candida albicans and Giardia lamblia, which became attached to the walls of the colon.

Probiotic bacteria can reduce the levels of toxic byproducts such as indole, skatole, and methane produced by the metabolic reaction of harmful bacteria to certain foods. Probiotics also assist the body's digestion of lactose and dietary carbohydrates. Finally, probiotic bacteria can aid the synthesis of B vitamins such as folic acid, niacin, pantothenic acid, and biotin.

It would be desirable to prepare a probiotic formulation which would act as a food supplement and assist in building the beneficial probiotic bacteria of the body's intestinal tract.

SUMMARY OF THE INVENTION

Accordant with the present invention, a beneficial probiotic formulation has surprisingly been discovered. The inventive probiotic formulation comprises the following ingredients:

a mixture of beneficial probiotic microflora, comprising lactobacillus acidophilus, bifidobacterium bifidum, lactobacillus salivarius, bifidobacterium infantis, and bifidobacterium longum;

fructooligosaccharides;

L-glutamine; and

N-acetyl glucosamine.

The probiotic formulation according to the present invention is useful as a food supplement, and additionally is particularly useful for reestablishing beneficial bacteria in the body's intestinal tract.

DETAILED DESCRIPTION OF THE PREFERRED EMBODIMENTS

The present invention is directed to a probiotic formulation useful as a food supplement and for reestablishing beneficial bacteria in the intestinal tract, comprising a mixture of beneficial probiotic microflora, comprising lactobacillus acidophilus, bifidobacterium bifidum, lactobacillus salivarius, bifidobacterium infantis, and bifidobacterium longum, fructooligosaccharides, L-glutamine, and N-acetyl glucosamine.

Lactobacillus acidophilus are well-known bacteria which inhabit the human small and large intestines. These are facultative anaerobic lactobacilli which produce lactic acid from interaction with carbohydrates.

Bifidobacterium bifidum are well-known bacteria found in human intestines and the female vagina. Levels of bifidobacteria decline with age and poor health. These bacteria produce acetic and lactic acids, and small amounts of formic acid, by fermentation with carbohydrates.

Lactobacillus salivarius are well-known bacteria commonly found in the human mouth and intestinal tract. These lactic acid producing bacteria create an acidic environment in which undesirable microorganisms are inhibited.

Bifidobacterium infantis are well-known bacteria typically found in the intestinal tract of human infants. These are anaerobic bacteria which produce acetic and lactic acids, as well as small amounts of formic acid.

Bifidobacterium longum are well-known bacteria found in the stools of human infants and adults. These bacteria form acetic, lactic, and formic acids by fermentation from a wide range of carbohydrates.

These five probiotic microflora may each, individually be present in the mixture of probiotic microflora at a concentration from about 20 to about 60 weight percent. The mixture of probiotic microflora may be present in the inventive probiotic formulation at a concentration from about 10 to about 50 weight percent. Preferably, the concentration ranges from about 30 to about 35 weight percent.

Fructooligosaccharides are well-known complexes of soluble fiber which act as a food for probiotic bacteria; especially for bifidobacteria. Human studies have indicated that fructooligosaccharides increase the levels of bifidobacteria and lower the stool pH, thereby indicating an increase in the numbers of beneficial bacteria in the colon. Fructooligosaccharides are present in the inventive probiotic formulation at a concentration ranging from about 10 to about 50 weight percent. Preferably, the concentration of fructooligosaccharides ranges from about 20 to about 30 weight percent.

L-glutamine is a well-known amino acid. Oral supplementation with L-glutamine is thought to inhibit adherence of Candida albicans to digestive tract surfaces. L-glutamine is present in the inventive probiotic formulation at a concentration ranging from about 15 to about 50 weight percent. Preferably, the concentration of L-glutamine ranges from about 30 to about 35 weight percent.

N-acetyl glucosamine is a well-known amino acid found in all tissues of the human body. N-acetyl glucosamine may be present in the inventive probiotic formulation at a concentration ranging from about 5 to about 20 weight percent. Preferably, the concentration of N-acetyl glucosamine ranges from about 10 to about 15 weight percent.

The aforementioned ingredients may be mixed together by conventional methods and formed into tablets for oral administration. Alternatively, the ingredients may be mixed together and placed into gelatin capsules. The inventive probiotic formulation may also contain conventional food supplement fillers and extenders such as, for example, rice flour. Conveniently, the probiotic formulation may be taken orally at a dosage rate ranging from about 100 milligrams to about 800 milligrams per day. Preferably, the dosage rate, effective as a food supplement and for reestablishing beneficial bacteria in the intestinal tract, ranges from about 200 milligrams to about 400 milligrams per day.

This invention is more easily comprehended by reference to the specific embodiments recited hereinabove which are representative of the invention. It must be understood, however, that the specific embodiments are provided only for the purpose of illustration, and that the invention may be practiced otherwise than as specifically illustrated without departing from its spirit and scope.

What is claimed is:

1. A probiotic formulation, consisting essentially of:
    a mixture of beneficial probiotic microflora, comprising:
        lactobacillus acidophilus, bifidobacterium bifidum, lactobacillus salivarius, bifidobacterium infantis, and bifidobacterium longum;
        fructooligosaccharides;
        L-glutamine; and
        N-acetyl glucosamine.

2. The probiotic formulation according to claim 1, wherein the probiotic microflora each, individually are present in the mixture of probiotic microflora at a concentration of about 20 weight percent.

3. The probiotic formulation according to claim 1, wherein the concentration of the mixture of probiotic microflora ranges from about 10 to about 50 weight percent.

4. The probiotic formulation according to claim 3, wherein the concentration of the mixture of probiotic microflora ranges from about 30 to about 35 weight percent.

5. The probiotic formulation according to claim 1, wherein the concentration of fructooligosaccharides ranges from about 10 to about 50 weight percent.

6. The probiotic formulation according to claim 5, wherein the concentration of fructooligosaccharides ranges from about 20 to about 30 weight percent.

7. The probiotic formulation according to claim 1, wherein the concentration of L-glutamine ranges from about 15 to about 50 weight percent.

8. The probiotic formulation according to claim 7, wherein the concentration of L-glutamine ranges from about 30 to about 35 weight percent.

9. The probiotic formulation according to claim 1, wherein the concentration of N-acetyl glucosamine ranges from about 5 to about 20 weight percent.

10. The probiotic formulation according to claim 9, wherein the concentration of N-acetyl glucosamine ranges from about 10 to about 15 weight percent.

11. A probiotic formulation, consisting essentially of:
    from about 10 to about 50 weight percent of a mixture of probiotic microflora, comprising lactobacillus acidophilus, bifidobacterium bifidum, lactobacillus salivarius, bifidobacterium infantis, and bifidobacterium longum;
    from about 10 to about 50 weight percent fructooligosaccharides;
    from about 15 to about 50 weight percent L-glutamine; and
    from about 5 to about 20 weight percent N-acetyl glucosamine.

12. The probiotic formulation according to claim 11, wherein the probiotic microflora each, individually are present in the mixture of probiotic microflora at a concentration of about 20 weight percent.

13. The probiotic formulation according to claim 11, wherein the concentration of the mixture of probiotic microflora ranges from about 30 to about 35 weight percent.

14. The probiotic formulation according to claim 11, wherein the concentration of fructooligosaccharides ranges from about 20 to about 30 weight percent.

15. The probiotic formulation according to claim 11, wherein the concentration of L-glutamine ranges from about 30 to about 35 weight percent.

16. The probiotic formulation according to claim 11, wherein the concentration of N-acetyl glucosamine ranges from about 10 to about 15 weight percent.

17. A probiotic formulation, consisting essentially of:
    from about 30 to about 35 weight percent of a mixture of probiotic microflora, comprising lactobacillus acidophilus, bifidobacterium bifidum, lactobacillus salivarius, bifidobacterium infantis, and bifidobacterium longum;
    from about 20 to about 30 weight percent fructooligosaccharides;
    from about 30 to about 35 weight percent L-glutamine; and
    from about 10 to about 15 weight percent N-acetyl glucosamine.

18. The probiotic formulation according to claim 17, where the probiotic microflora each, individually are present in the mixture of probiotic microflora at a concentration of about 20 weight percent.

* * * * *